United States Patent [19]

Umezawa et al.

[11] Patent Number: 4,547,492

[45] Date of Patent: Oct. 15, 1985

[54] 1-N-(ω-AMINO-α-HYDROXYALKANOYL-2′,3′-DIDEOXYKANAMYCIN A AND PHARMACEUTICAL COMPOSITION CONTAINING SAME

[75] Inventors: Hamao Umezawa; Sumio Umezawa, both of Tokyo; Tsutomu Tsuchiya; Toshio Yoneta, both of Yokohama; Shunzo Fukatsu, Tokyo, all of Japan

[73] Assignee: Zaidan Hojin Biseibutsu Kagaku Kenkyu Kai, Japan

[21] Appl. No.: 639,392

[22] Filed: Aug. 10, 1984

[30] Foreign Application Priority Data

Aug. 15, 1983 [JP] Japan ................... 58-147965

[51] Int. Cl.$^4$ ............. A61K 31/71; C07H 15/22
[52] U.S. Cl. ................. 514/41; 536/13.7; 536/13.8

[58] Field of Search .......... 424/180; 536/13.7, 13.8; 514/41

[56] References Cited

U.S. PATENT DOCUMENTS 4,104,372  8/1978  Umezawa et al. ............. 536/13.8
4,160,082  7/1979  Million et al. ............... 536/13.8
4,298,727  11/1981 Umezawa et al. ............. 536/13.8

Primary Examiner—Johnnie R. Brown
Attorney, Agent, or Firm—Larson and Taylor

[57] ABSTRACT

1-N-(L-3-amino-2-hydroxypropionyl)-2′,-3′-dideoxykanamycin A and 1-N-(L-4-amino-2-hydroxybutyryl)-2′,3′-dideoxykanamycin A are now provided which each is a new compound useful as antibacterial agent. The new compounds each is produced by acylating the 1-amino group of 2′,3′-dideoxykanamycin A with L-3-amino-2-hydroxypropionic or L-4-amino-2-hydroxybutyric acid.

4 Claims, No Drawings

1-N-(ω-AMINO-α-HYDROXYALKANOYL-2′,3′-DIDEOXYKANAMYCIN A AND PHARMACEUTICAL COMPOSITION CONTAINING SAME

SUMMARY OF THE INVENTION

This invention relates to 1-N-(L-3-amino-2-hydroxypropionyl)- and 1-N-(L-4-amino-2-hydroxybutyryl)-2′,3′-dideoxykanamycins A which each is a new compound useful as semi-synthetic aminoglycoside antibiotics. This invention also relates to a process for the production of these new compounds, as well as an antibacterial composition containing at least one of these new compounds as active ingredient.

BACKGROUND OF THE INVENTION

We, the present inventors, have made study about various deoxy derivatives of an aminoglycoside antibiotic, kanamycin A, and we or some of us, as joint-inventors, have succeeded to synthesize 3′-deoxykanamycin A (U.S. Pat. No. 4,104,372); 3′,4′-dideoxykanamycin A (U.S. Pat. No. 4,298,727); 5,2′,3′,4′,4″,6″-hexadeoxykanamycin A (U.S. patent application Ser. No. 532,058, now U.S. Pat. No. 4,486,419); and 2′-deoxykanamycin A (U.S. Pat. No. 4,455,419). As a result of our further study, we have also succeeded in synthesizing 2′,3′-dideoxykanamycin A which we have never synthesized, by a method comprising preparing a tetra-N-protected and 4′,2″,4″,6″-tetra-O-protected kanamycin A derivative from kanamycin A, converting this derivative into an N,O-protected 2′,3′-dideoxy-2′-eno-kanamycin A derivative, reducing this 2′-eno-kanamycin A derivative into an N,O-protected 2′,3′-dideoxykanamycin A derivative, and removing all the protective groups from the latter derivative to produce 2′,3′-dideoxykanamycin A (our pending Japanese patent application No. 213329/82 and its corresponding Japanese patent application first publication "Kokai" No. 104396/84). We have now been aware of the fact that 2′,3′-dideoxykanamycin A was already disclosed in U.S. Pat. No. 4,171,356 issued Oct. 16, 1979. Furthermore, we have been aware that various 1-N-(ω-amino-α-hydroxyalkanoyl) derivatives were synthesized from kanamycins A, B and C as well as kanamycin deoxyderivatives such as 3′-deoxykanamycin A, 3′-deoxykanamycin B, 3′,4′-dideoxykanamycin A, 3′,4′-dideoxykanamycin B, 5,2′,3′,4′,4″,6″-hexadeoxykanamycin A and the like (see eg. U.S. Pat. No. 3,781,268; U.S. Pat. No. 3,939,143; U.S. Pat. No. 4,001,208; U.S. Pat. No. 4,104,372; U.S. Pat. No. 4,107,424; U.S. Pat. No. 4,297,485; U.S. Pat. No. 4,298,727; U.S. patent application Ser. No. 532,058; and others).

Now, we have made further research in an attempt to provide such a new useful derivative of 2′,3′-dideoxykanamycin A which is active against various resistant-strains of bacteria and which is also active against such resistant bacteria as is expected to occur in the future owing to extensive use of known aminoglycoside antibiotics and known semi-synthetic aminoglycoside antibiotics in clinics. We have now succeeded in synthesizing 2′,3′-dideoxykanamycin A derivative, 1-N-(L-4-amino-2-hydroxybutyryl)-2′,3′-dideoxykanamycin A and 1-N-(L-3-amino-2-hydroxypropionyl)-2′,3′-dideoxykanamycin A, and have now confirmed that each of these compounds is a new semi-synthetic aminoglycoside antibiotic exhibiting a useful high antibacterial activity against various resistant bacteria.

DETAILED DESCRIPTION OF THE INVENTION

According to a first aspect of this invention there is provided a 2′,3′-dideoxykanamycin A derivative represented by the formula

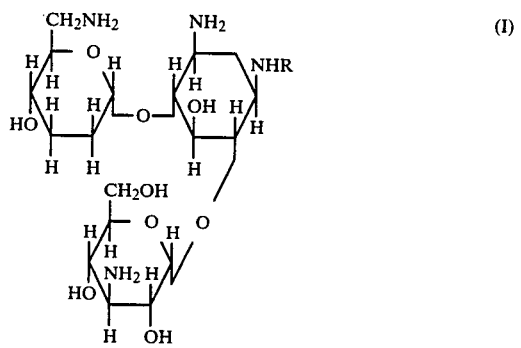

wherein R denotes an L-3-amino-2-hydroxypropionyl group

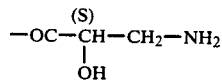

or an L-4-amino-2-hydroxylbutyryl group

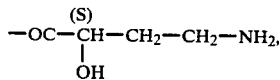

and an acid addition salt thereof.

The 2′,3′-dideoxykanamycin A derivative of formula (I) according to this invention is usually obtained in the form of the free base or a hydrate or a carbonate thereof, but it may readily be converted into the form of a non-toxic acid addition salt in a known manner by reacting with a non-toxic acid. The acids used for formation of the acid addition salts include a pharmaceutically acceptable inorganic acids such as hydrochloric acid, sulfuric acid, phosphoric acid, nitric acid and the like, as well as a pharmaceutically acceptable organic acid such as acetic acid, malic acid, citric acid, ascorbic acid, methanesulfonic acid and the like.

The new compounds of the formula (I) of this invention, namely 1-N-(L-4-amino-2-hydroxybutyryl)-2′,3′-dideoxykanamycin A (abbreviated as AHDK hereinafter) and 1-N-(L-3-amino-2-hydroxy-propionyl)-2′,3′-dideoxykanamycin A (abbreviated as ISDK hereinafter) give antibacterial spectra (MIC.) as shown in the following Table 1, from which it is clear that the new compounds of this invention each exhibits a high antibacterial activity against the resistant bacteria. For comparison purpose, the minimum inhibitory concentrations (MIC.) of 1-N-(L-4-amino-2-hydroxybutyryl)-kanamycin A, namely amikacin and of 2′,3′-dideoxykanamycin A (abbreviated as DKA) are also shown in Table 1.

The minimum inhibitory concentrations (mcg/ml) of these kanamycin A derivatives against the various bacteria were determined according to a standard serial dilution method on a nutrient agar medium at 37° C., the estimation being made after 18 hours incubation.

TABLE 1

| Test organisms | | MIC. (mcg/ml) | | | |
|---|---|---|---|---|---|
| | | ISDK | AHDK | Amikacin (comparative) | DKA (comparative) |
| Staphylococcus aureus | 209P | 0.20 | 0.10 | 0.78 | 1.56 |
| " | Ap 01 | 0.78 | 0.39 | 1.56 | 3.13 |
| Bacillus subtilis | PCI 219 | 0.39 | 0.20 | 0.39 | 0.39 |
| Escherichia coli | J5R11-2 | 0.78 | 0.78 | 1.56 | 3.12 |
| " | ML 1629 | 1.56 | 1.56 | 1.56 | 1.56 |
| " | ML 1630 | 3.13 | 1.56 | 3.13 | 3.13 |
| " | ML R 81 | 1.56 | 1.56 | 1.56 | 3.13 |
| Serratia sp. 4 | | 1.56 | 1.56 | 3.13 | — |
| Proteus rettgeri | GN 311 | 0.39 | 0.39 | 0.39 | — |
| Pseudomonas aeruginosa | A3 | 0.78 | 0.78 | <0.20 | 1.56 |
| " | H9 | 3.13 | 3.13 | 6.25 | 6.25 |
| " | B-13 | 12.5 | 12.5 | 6.25 | 12.5 |
| " | K-Ps 102 | 6.25 | 6.25 | 6.25 | 6.25 |
| Serratia marcescens | I-0111 | 3.13 | 6.25 | 25 | — |
| " | I-0115 | 3.13 | 6.25 | 50 | — |
| " | I-0139 | 6.25 | 12.5 | 100 | — |
| " | I-0162 | 6.25 | 6.25 | 50 | — |

As will be clear from Table 1, the new compounds of this invention effectively inhibit the growth of many kinds of bacterial strains. Besides, the new compounds of this invention have low acute toxicity to animals, as estimation of acute toxicity by intravenous injection in mice has revealed that AHDK showed an $LD_{50}$ value of 326 mg (potency)/kg and ISDK showed an $LD_{50}$ value of 240 mg (potency)/kg. Accordingly, the new compounds of this invention are useful in therapeutic treatment of various kinds of gram-positive and gram-negative bacterial infections.

The new compound of formula (I) according to this invention and its pharmaceutically acceptable acid addition salt may be administered orally, intraperitoneally, intravenously, subcutaneously or intramuscularly using any pharmaceutical form known to the art for such administration and in a similar manner to the known kanamycins. For instance, the new compound of this invention may be administered orally using any pharmaceutical form known to the art for oral administration. Examples of the pharmaceutical forms for oral administration are powders, capsules, tablets, syrup and the like. A suitable dose of the new compound of this invention for effective treatment of bacterial infections is in a range of 0.2 to 2 g. per person a day when it is given orally. It is preferred that said dose should be orally administered in three to four aliquots per day. The new compound of this invention may also be administered by intramuscular injection at a dosage of 100 to 1000 mg per person two to four times a day. Moreover, the new compound of this invention may be formulated into an ointment for external application which contains the active compound at a concentration of 0.5~5% by weight in mixture with a known ointment base such as polyethylene glycol. Furthermore, the new compound of this invention is useful for sterilization of surgical instruments and sanitary materials.

According to a second aspect of this invention there is provided an antibacterial composition comprising as active ingredient the compound of formula (I) or a pharmaceutically acceptable acid addition salt thereof in an antibacterially effective amount to inhibit the growth of bacteria, in combination with a carrier for the active ingredient compound.

Generally speaking, the production of the compound of formula (I) according to this invention may be achieved by acylating the 1-amino group of 2',3'-dideoxykanamycin A of the formula

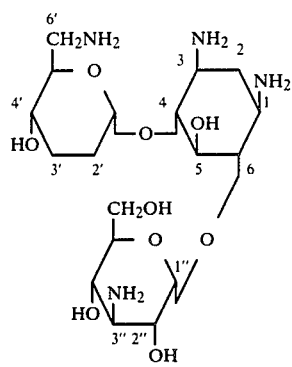

(II)

or such a partially N-protected 2',3'-dideoxykanamycin A derivative in which some or all of the three amino groups other than the 1-amino group each has been protected by a known amino-protecting group, with L-3-amino-2-hydroxypropionic acid or L-4-amino-2-hydroxybutyric acid represented by the formula

R'COOH    (III)

wherein R' denotes a 2-amino-1-hydroxyethyl group or a 3-amino-1-hydroxypropyl group. The ω-amino-α-hydroxyalkanoic acid of formula (III) as the acylating agent may also be in the form of its reactive acid derivative which reacts as a functional equivalent of the compound of formula (III) and may be, for example, in the form of an active ester, an active azide, an active acid anhydride, a mixed acid anhydride or the like of the alkanoic acid compound (III). Besides, the amino group of the ω-amino-α-hydroxyalkanoic acid of formula (III) may preferably be blocked with an amino-protecting group.

The 1-N-acylation of the starting 2',3'-dideoxykanamycin (II) may be carried out in a known manner. When either one or both of the starting compound (II) and the acylating agent compound of formula (III) have been N-protected, the resulting 1-N-acylated product normally contains therein amino groups which remain protected. Accordingly, it is then necessary to remove the remaining amino-protective groups from such 1-N-acylated product containing the protected amino groups, in order to afford the desired compound of formula (I).

According to a further aspect of this invention there is provided a process for the production of 1-N-(L-3-amino-2-hydroxypropionyl)- or 1-N-(L-4-amino-2-hydroxybutyryl)-2′,3′-dideoxykanamycin A of formula (I), which comprises the steps of:

(i) acylating the 1-amino group of 2′,3′-dideoxykanamycin A or a partially N-protected derivative thereof represented by the formula

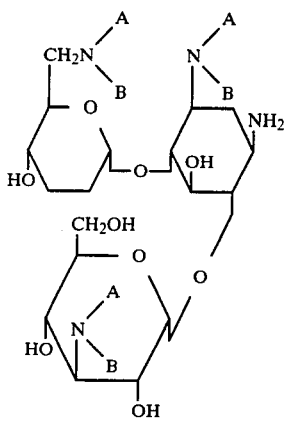
(II′)

wherein A is a hydrogen atom and B is a hydrogen atom, or A is a hydrogen atom and at least one B is a monovalent amino-protecting group but the other B(s) is or are each a hydrogen atom, or at least one pair of A and B taken together form a di-valent amino-protecting group but the other A and B are each a hydrogen atom, by reacting with L-3-amino-2-hydroxypropionic or L-4-amino-2-hydroxybutyric acid or an amino-protected derivative thereof represented by the formula

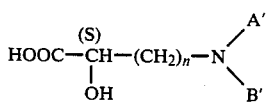
(III′)

wherein A′ is a hydrogen atom and B′ is a hydrogen atom or a mono-valent amino-protecting group, or A′ and B′ taken together form a di-valent amino-protecting group and n is an integer of 1 or 2, or a reactive acid derivative thereof to produce the 1-N-acylated product represented by the formula

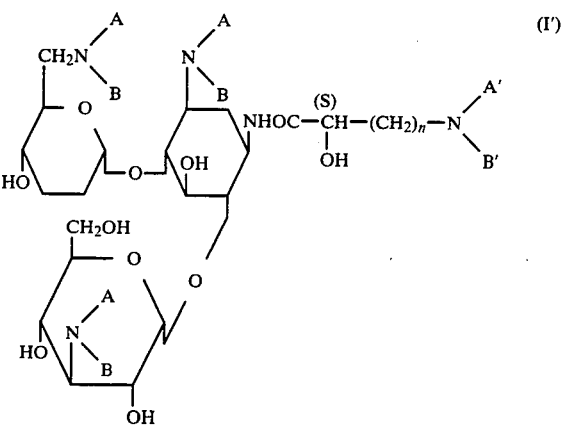
(I′)

wherein A, B, A′, B′ and n are as defined above, and (ii) removing the remaining amino-protecting groups, where they exist, from the 1-N-acylated product of formula (I′) to produce the desired compound of formula (I).

In carrying out the present process according to this invention, it is possible to use as the starting compound 2′,3′-dideoxykanamycin A in formula (II) of which all the four amino groups are not protected, in the form of the free base or an acid addition salt thereof such as the hydrochloride or sulfate. However, it is preferred to employ as the starting compound a partially N-protected derivative of 2′,3′-dideoxykanamycin A in which all or some of the amino groups other than the 1-amino group have been protected with known amino-protecting groups and which may be prepared by introduction of the known amino-protecting groups into 2′,3′-dideoxykanamycin A by means of a known amino-protecting technique.

In general, an ordinary amino-protecting group may be used as the amino-protecting groups for the protection of some or all of the amino groups other than the 1-amino group of the starting 2′,3′-dideoxykanamycin A of formula (II). The available amino-protecting groups include an alkyloxycarbonyl group such as tert-butoxycarbonyl and tert-amyloxycarbonyl; a cycloalkyloxycarbonyl group such as cyclohexyloxycarbonyl; an aralkyloxycarbonyl group such as benzyloxycarbonyl; an acyl group such as trifluoroacetyl and o-nitrophenoxyacetyl; a phosphinothioyl group such as diphenylphosphinothioyl and dimethylphosphinothioyl; a phosphinyl group such as diphenylphosphinyl, and the like. Preferred examples of the di-valent amino-protecting group include phthaloyl group and a group of Schiff base type such as salicylidene. The introduction of the amino-protecting group of these kinds may be conducted by reacting the compound of formula (II) with an appropriate known reagent for introduction of the amino-protecting group which may be in the form of an acid halide, acid azide, active ester or acid anhydride and the like, in the manner known in the conventional synthesis of peptides. By chosing the quantity of the reagent for introduction of the amino-protecting group employed in a proportion of 0.5 to 6 mol. per mol. of the compound of formula (II), it is possible to prepare a mixture of different, partially amino-protected derivatives (II′) at any ratio, due to the difference in the reactivity of the respective amino groups of the compound (II).

In the process of producing the new compound according to this invention, it is feasible to employ as the starting compound an amino-protected 2',3'-dideoxykanamycin A derivative in which all or some of the amino groups other than the 1-amino group have been protected, for example, a 3,6',3"-tri-N-protected derivative, a 3,6'-di-N-protected derivative, 6',3"-di-N-protected derivative or a 6'-mono-N-protected derivative. Besides, a mixture of two or more of these partially N-protected derivatives may, without being purified or isolated, be used for the 1-N-acylation step of the present process.

In order to ensure that the desired compound of the general formula (I) can be produced in a high yield according to the process of this invention, it needs only that just the 1-amino group of the starting compound of formula (II) be preferentially acylated with the ω-amino-α-hydroxyalkanoic acid of formula (III'). Accordingly, it will be evident that most preferably, a protected derivative of the compound (II) in which all the amino groups other than the 1-amino group have been protected, namely a 3,6',3"-tri-N-protected derivative of the compound (II) is employed as the starting substance to be 1-N-acylated in the present process.

To prepare a 3,6',3"-tri-N-protected 2',3'-dideoxykanamycin A derivative of formula (II') from the compound of formula (II), the following procedure may conveniently be used, for instance. Thus, a 3,6'-di-N-protected derivative of formula (II') is prepared at first from the compound (II) either according to a known method of U.S. Pat. No. 4,136,254 (corresponding to Japanese patent application first publication "Kokai" No. 153944/77) comprising reacting 2',3'-dideoxykanamycin A with cation of a di-valent transition metal such as copper (II), nickel (II), cobalt (II) and others for the formation of a metal complex, reacting this metal complex with an acylation reagent known as an amino-protective group-introducing agent for the protective N-acylation of all the amino groups other than the 1- and 3"-amino groups of the kanamycin A moiety in the 2',3'-dideoxykanamycin A-metal complex [these 1- and 3"-amino groups having been blocked by complexing with the di-valent transition metal cation], and then removing the di-valent metal cation from the thus protectively N-acylated 2',3'-dideoxykanamycin A-metal complex, eg. by treatment with a cation-exchange resin or by treatment with hydrogen sulfide to afford a 3,6'-di-N-acylated derivative of 2',3'-dideoxykanamycin A; or according to a method of claim 1 of our U.S. Pat. No. 4,297,485 (corresponding to our Japanese patent application first publication "Kokai" No. 64598/80; Japanese patent application No. 138402/78) comprising reacting 2',3'-dideoxykanamycin A with zinc cation in stead of the above-mentioned di-valent transition metal cation and subsequently processing the resultant zinc complex in a similar way to the above-mentioned known method of U.S. Pat. No. 4,136,254. In this way, a 3,6'-di-N-protected 2',3'-dideoxykanamycin A derivative of formula (II') can be prepared from the compound of formula (II) in a high yield. The 3"-amino group of this 3,6'-di-N-protected derivative (II') thus prepared can further be protected according to a selective 3"-N-acylation method of claim 15 of our U.S. Pat. No. 4,297,485 (also corresponding to Japanese patent application first publication "Kokai" No. 164696/80; Japanese patent application No. 73064/79) for the production of such an amino-protected derivative of an aminoglycoside antibiotic of which all the amino groups other than the 1-amino group have been protected selectively, so that a 3,6',3"-tri-N-protected derivative of the compound (II) can be prepared in a high yield. In accordance with the selective 3"-N-acylation method of the claim 15 of U.S. Pat. No. 4,297,485, the above-mentioned 3,6'-di-N-protected derivative of formula (II') is reacted with a formic acid alkyl ester, a di-halo- or tri-halo-alkanoic acid alkyl ester or N-formylimidazole as the acylation agent, whereby the 3"-amino group can be acylated selectively with the formyl or di- or haloalkanoyl residue of said acylation agent in a high yield, without involving the acylation of the 1-amino group of said 3,6'-di-N-protected derivative. The 3,2',3"-tri-N-acylated derivative, for example, 3,6'-di-N-tert-butoxycarbonyl- or 3,6'-di-N-benzyloxycarbonyl-3"-N-trifluoroacetyl derivative of 2',3'-dideoxykanamycin A may be obtained by applying the above-mentioned method of the U.S. Pat. Nos. 4,136,254 and 4,297,485 and is a most preferred starting compound to be 1-N-acylated with the ω-amino-α-hydroxyalkanoic acid (III') in the 1-N-acylation step of the present process.

In the process of this invention, the 1-amino group of the compound of formula (II) or the 1-amino group of the partially amino-protected derivatives (II') thereof, either isolated or in mixture with two or more of them, is acylated with the ω-amino-α-hydroxyalkanoic acid of formula (III') of which the amino group is either not protected or has been protected. This ω-amino-α-hydroxyalkanoic acid may be L-3-amino-2-hydroxypropionic acid (i.e. the compound of formula (III') where n is 1; A' and B' are the hydrogen atoms) or L-4-amino-2-hydroxybutyric acid (i.e. the compound of formula (III') where n is 2; A' and B' are the hydrogen atoms). In the process of this invention, the 1-N-acylation of the compound (II) or (II') with the ω-amino-α-hydroxyalkanoic acid (III') may be conducted according to any of the conventional methods for the synthesis of peptides, for instance, according to the known dicyclohexylcarbodiimide method, the known mixed acid anhydride method, the known azide method or the active ester method and the like, using the ω-amino-α-hydroxyalkanoic acid (III') as such or in the form of its reactive acid derivative (as a functional equivalent thereof). For the amino-protecting group for protection of the amino group of the ω-amino-α-hydroxyalkanoic aicd (III') may be employed such as amino-protecting group which is the same as or different from the one present in the starting compound (II'). Particularly, a preferred amino-protecting group for this purpose is tert-butoxycarbonyl group or p-methoxybenzyloxycarbonyl group which is easily removable by treatment with aqueous trifluoroacetic acid or acetic acid or with diluted aqueous hydrochloric acid. Benzyloxycarbonyl group which is removable by a conventional hydrogenolysis in the presence of a catalyst such as palladium of platinum oxide is also a convenient N-protecting group.

The 1-N-acylation of the starting compound (II) or (II') in the present process may desirably be carried out in an aqueous organic solvent according to the active ester method using the ω-amino-α-hydroxyalkanoic acid compound (III') in the form of its active ester. For example, N-hydroxysuccinimide ester of L-4-tert-butoxycarbonylamino-2-hydroxybutyric acid may preferably be used as the active ester which may be prepared by a conventional method of preparing the active ester. This active ester may preferably be used in a proportion of from 0.5 to 3 molar equivalents and preferably of from 1 to 1.5 molar equivalents per mol of the starting compound (II) or (II') to be 1-N-acylated. The aqueous organic solvent used as the reaction medium may be a water-miscible organic solvent such as dioxane, 1,2-dimethoxyethane, dimethylformamide, tetrahydrofuran, triethylamine and the like. The 1-N-acylation may be effected at ambient temperature but generally at a temperature of 0° C.~90° C., preferably of 20° C.~30° C. and for a reaction time of 10 minutes to 18 hours and preferably 30 minutes to 60 minutes.

When the 1-N-acylation in the present process is conducted using as the starting compound such a partially amino-protected derivative (II') in which some, but not all, of the amino groups other than the 1-amino group has or have been protected, for example, the 6'-N-protected derivative of the starting compound (II'), the N-acylation products as formed may partially be purified by a column chromatography, for example, on silica gel so that the unreacted starting material is removed, giving a mixture of the desired 1-N-monoacylated product with the otherwise N-acylated products, as the case may be in the synthesis of habekacin, namely 1-N-[(S)-4-amino-2-hydroxybutyryl]-3',4'-dieoxykanamycin B as described in the specification of U.S. Pat. No. 4,107,424. These mixed acylation products may, without being purified and/or isolated, be subjected immediately to the subsequent de-protecting step of the present process, followed by the step of purification and isolation so that the desired 1-N-monoacylated product is obtained.

In the second step of the process of this invention, the 1-N-acylated product (including the mixed acylation products) as obtained in the 1-N-acylation step of the present process is subjected to the removal of the amino-protecting groups, if these are still remaining in the 1-N-acylated product. The removal of the protecting groups is effected by a conventional deprotecting technique. Thus, the amino-protecting group of the alkoxycarbonyl type is removed by acid hydrolysis with an aqueous solution of trifluoroacetic acid or acetic acid and the like or with a diluted aqueous solution of an inorganic acid such as hydrochloric acid. The aralkyloxycarbonyl group such as benzyloxycarbonyl may easily be removed by an ordinary catalytic reduction (hydrogenolysis). When phthaloyl group is remaining as the amino-protecting group, it can be removed by treating in a solution of hydrazine hydrate in a lower alkanol such as methanol.

It is convenient to conduct the synthesis of the new compound (I) of this invention according to such a particular multi-stage procedure as described below which starts with 2',3'-dideoxykanamycin A and utilizes the selective N-protection methods of U.S. Pat. No. 4,297,485 (corresponding to Japanese patent application first publication "Kokai" No. 164696/80).

Thus, according to this particular procedure, the starting 2',3'-dideoxykanamycin A (Compound 1) and zinc acetate are dissolved in a mixture of water and dimethylformamide (DMF), and the 2',3'-dideoxykanamycin A-zinc complex as formed is reacted with two or more molar proportion of N-benzyloxycarbonyloxysuccinimide

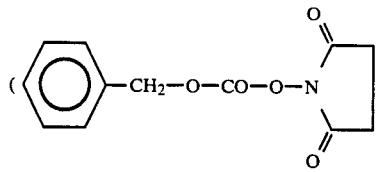

as an amino-protective group-introducing reagent) to protect the 3- and 6'-amino groups of the kanamycin A moiety of the zinc complex with the benzyloxycarbonyl groups, followed by removing the zinc cation from the resultant 3,6'-di-N-benzyloxycarbonylated 2',3'-dideoxykanamycin A-zinc complex to give 3,6'-di-N-benzyloxycarbonyl-2',3'-dideoxykanamycin A (Compound 2) (... Stage 1). Compound 2 is then reacted with ethyl trifluoroacetate in DMF to protect the 3''-amino group of Compound 2 with the trifluoroacetyl group, affording 3,6'-di-N-benzyloxycarbonyl-3''-N-trifluoroacetyl-2',3'-dideoxykanamycin A (Compound 3) (... Stage 2). Further, Compound 3 is reacted with 4-N-benzyloxycarbonyl-L-4-amino-2-hydroxybutyric acid N-hydroxysuccinimide ester (for the production of AHDK) or with 3-N-benzyloxycarbonyl-L-3-amino-2-hydroxypropionic acid N-hydroxysuccinimide ester (for the production of ISDK) in aqueous tetrahydrofuran (THF) in the presence of sodium carbonate so that the 1-amino group of Compoud 3 is acylated with the 4-N-benzyloxycarbonyl-L-4-amino-2-hydroxybutyryl group (for the production of AHDK) or with the 3-N-benzyloxycarbonyl-L-3-amino-2-hydroxypropionyl group (for the production of ISDK) (... Stage 3), whereby there is formed 1-N-(N-benzyloxycarbonyl-L-4-amino-2-hydroxybutyryl)- or 1-N-(N-benzyloxycarbonyl-L-3-amino-2-hydroxypropionyl)-3,6'-di-N-benzyloxycarbonyl-3''-N-trifluoroacetyl-2',3'-dideoxykanamycin A (Compound 4) as the 1-N-acylation product.

Compound 4 is then subjected to the deprotecting treatment by acidic or alkaline hydrolysis for removal of the amino-protecting trifluoroacetyl group therefrom and subsequently by catalytic hydrogenolysis in the presence of a palladium catalyst for removal of the amino-protecting benzyloxycarbonyl groups therefrom (... Stage 4), so that the desired compound of formula (I), namely AHDK or ISDK is afforded.

The above-mentioned particular procedure of producing the compound of this invention is depicted in the following chart where Z denotes a benzyloxycarbonyl group:

PRODUCTION CHART

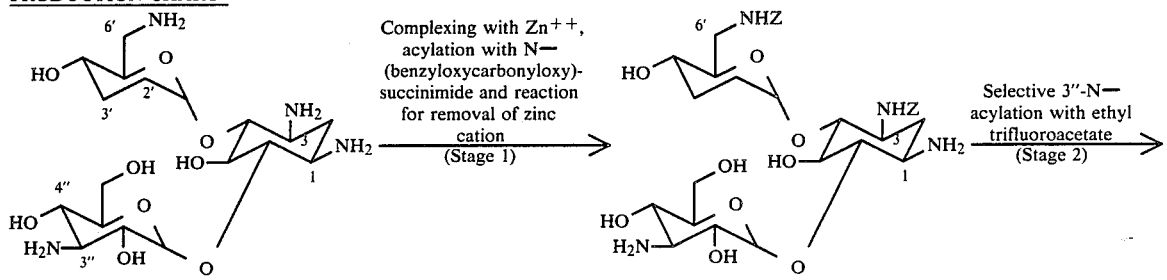

(Compound 1)

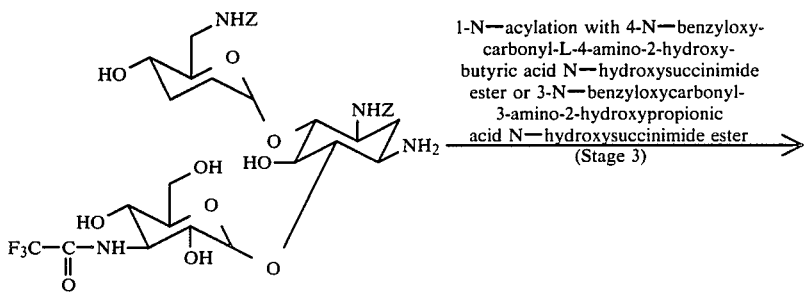

(Compound 2)

(Compound 3)

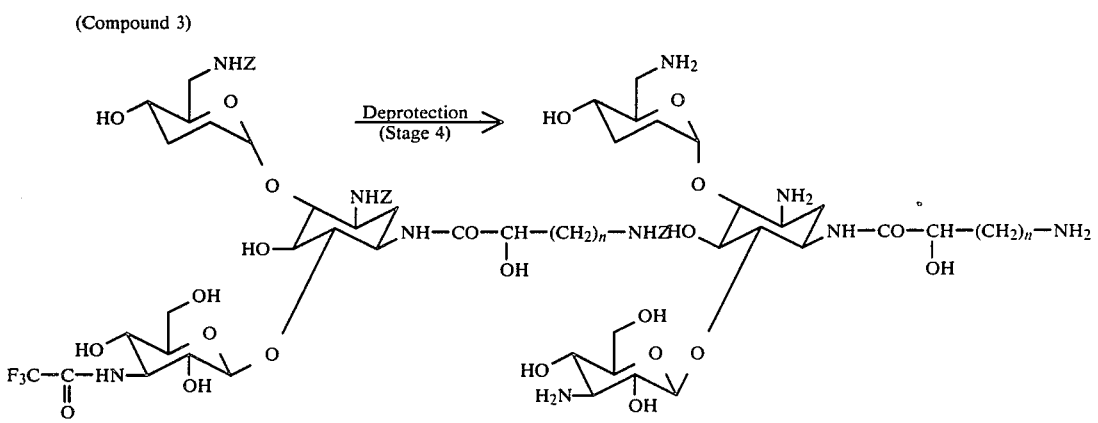

(Compound 4) (n = 1 or 2)     (The desired compound (I)) (n = 1 or 2)

A detailed description will now be made about the above particular procedure according to the Chart.

The synthesis of the starting 2',3'-dideoxykanamycin A is disclosed in the specification of our Japanese patent application first publication "Kokai" No. 104396/84 (Japanese patent application No. 213329/82) or U.S. Pat. No. 4,171,356. Stage 1 is conducted for the purpose of preferentially introducing the amino-protecting groups into the 3- and 6'-amino groups of the starting Compound 1. For this purpose, Compound 1 is reacted with the zinc cation at first in Stage 1, and the presence of zinc cation invokes the reaction of complexing the zinc cation with the amino groups (at the 1- and 3"-positions) other than the 3- and 6'-amino groups of Compound 1, whereby the 1- and 3"-amino groups of Compounds 1 can be blocked in the form of the zinc complex. Upon this, the zinc cation is supplied as a zinc salt to the reaction system where the zinc complex is to be formed. For this zinc salt, there may be used any zinc salt which may be produced by reaction of zinc cation with an ordinary inorganic acid or organic acid. In general, however, a zinc salt with a weak acid, such as zinc acetate is preferred because usually a metal complex containing an amino group is more stable with such a complex of the metal and free amino group than with such a complex of the metal and an ammonium-type amine. Even when a zinc salt with a strong acid, such as zinc chloride is used, a 2',3'-dideoxykanamycin A-zinc complex may be formed without needing any further means, but it is then desirable that a quantity of weakly alkaline sodium acetate should be present additionally in the reaction system where the zinc complex is to be formed.

As long as the total molar quantity of the zinc salt as supplied to the reaction system is at least equal to the molar quantity of 2',3'-dideoxykanamycin A, the zinc complex-forming reaction can proceed to a desired extent. As this complex-forming reaction is an equilibrium reaction, however, it is preferred to use the zinc salt in a quantity of substantially more than 1 mol per mol of the 2',3'-dideoxykanamycin A so that the equilibrium of the complex-forming reaction can be shifted in favor of the formation of the zinc complex. Favorable yield of the zinc complex may be obtained when using the zinc salt in a quantity of about 2.3 to 6 mol. per mol of the starting kanamycin A compound, but it is most preferable in practice to use the zinc salt in a quantity of 4 to 5 mol. per mol of the kanamycin A compound. The time required for the zinc complex-forming reaction after the addition of the zinc salt can vary depending on the nature of the solvent used, but that time may be in a range of from "instantaneously" (when using aqueous organic solvent) to 20 hours. The complex-forming reaction may proceed completely at ambient temperature, but heating or cooling may be done, if desired.

In this way, a solution or suspension containing the complex of 2',3'-dideoxykanamycin A with zinc cation may be prepared, with which may then be admixed and reacted such an acylation reagent having an acyl group to be introduced as the amino-protecting group.

The acylation reagent employed in Stage 1 for introduction of the amino-protecting group may generally be such one having an acyl group which is ultimately cleavable from the protected amino groups through catalytic hydrogenolysis. Such an acylation reagent containing benzyloxycarbonyl group is preferred, and an example of the N-protecting acylation reagent employed in the particular procedure of the Chart shown above is carbonyloxysuccinimide.

The acylation reagent for the protection of the amino groups (actually the non-chelated amino groups of the zinc complex) may be used as such or in the form of a solution in an organic solvent such as tetrahydrofuran (THF) or dimethylsulfoxide (DMSO) or a mixture of THF and DMSO. The molar quantity of the N-protecting acylation reagent used may normally be equal to or in a slight excess over the number of the non-chelated amino groups to be acylated and so protected, but the acylation reagent may occasionally be added in a molar quantity of up to 3 times higher than the number of the non-chelated amino groups which are present in the zinc complex. The acylation reagent used may be added at once or in portions over a duration of 2 to 3 hours, but it may usually be added over a time of from 30 minutes to 1 hour. The acylation reaction for the amino-protecting purpose may be carried out at a temperature of from −20° C. to 100° C. but is usually effected at a temperature in the range of from 0° C. to ambient temperature. In some cases, however, the temperature may be kept low at the initial time of addition of the acylation reagent for the amino-protecting purpose and then be elevated gradually as the acylation proceeds. The acylation reaction for the amino-protecting purpose may normally be effected in situ in the same solvent which was employed for the formation of the zinc complex and in which the formation of the zinc complex took place. This acylation of the zinc complex produces the N-acylated zinc complex by acylating the non-chelated 3- and 6'-amino groups of the 2',3'-dideoxykanamycin A-zinc complex which have been remaining un-chelated with the zinc cation.

The N-acylated zinc complex so prepared is then recovered from the N-protecting acylation reaction solution and is subsequently be subjected to the step of removing the zinc cation from the N-acylated zinc complex in order to yield the 3,6'-di-N-acylated 2',3'-dideoxykanamycin A which is free from the complexing zinc. For removal of the zinc from the N-acylated zinc complex, it is necessary to treat the latter with a suitable agent which can remove the zinc cation from said N-acylated zinc complex. For this purpose, there are many available methods. A first suitable method is to react the N-acylated zinc complex with a zinc-precipitating agent which is capable of converting the zinc cation into a water-insoluble zinc compound. Such zinc-precipitating agents may be hydrogen sulfide or sodium sulfide. A second suitable method is to dilute said acylation reaction solution with a suitable liquid diluent and thereby deposit the N-acylated zinc complex as an oil or a solid matter, dissolve this oil or solid matter into a volume of a suitable aqueous organic solvent and pass the resultant solution through a column of a cation-exchange resin, an anion-exchange resin, a chelate-exchange resin or a water-insoluble polymer containing any functional groups capable of combining with a metal, followed by development of the column with a suitable aqueous organic solvent containing or not containing a proportion of acid or base (see U.S. Pat. No. 4,297,485).

In particular, however, it is convenient to recover the aforesaid N-acylated zinc complex (namely, the N-acylated 2',3'-dideoxykanamycin A product still remaining in the form of the zinc complex) from the acylation reaction solution by extracting the latter with a suitable organic solvent and then concentrating the organic extract to a smaller volume or to dryness. The syrupy or solid residue so obtained may then be treated with a suitable zinc-removing agent as mentioned above.

As an alternative method, it is also convenient to admix the acylation reaction solution with a suitable liquid diluent and thereby deposit an oily or solid mixture therefrom, to dissolve the whole mixture so deposited into a suitable aqueous organic solvent (where said mixture as the whole is soluble or partially soluble in water), and to pass the resultant solution through a column of a cation-exchange resin so that the zinc cation can be removed from the N-acylated zinc complex and concurrently the desired N-acylated, protected 2',3'-dideoxykanamycin A derivative (Compound 2) can be recovered chromatographically. When this alternative method is carried out using a cation-exchange resin containing carboxylic functions, it is practical to dissolve said oily or solid mixture (as deposited by dilution of said acylation reaction solution with liquid diluent) into a volume of a suitable aqueous organic solvent, for example, a mixture of water and methanol containing a varying proportion, e.g. of 10~90% (by volume) of water or a mixture of water and dioxane containing a varying proportion, e.g. 10~90% (by volume) of water, to charge the resultant solution in a column of the cation-exchange resin, to wash the resin column first with an additional volume of the above-mentioned aqueous organic solvent and then to elute the resin column using as the development solvent such a further volume of the above-mentioned aqueous organic solvent comprising a proportion of a base which may mainly be ammonium hydroxide. The proportion of the base in the development solvent used may suitably be in a range of 0.01~5% (by weight). The zinc cation and the desired N-acylated, protected 2',3'-dideoxykanamycin A derivative (Compound 2) can be separated from each other in the development process owing to their different powers of being adsorbed by the cation-exchange resin, because the zinc cation and the N-acylated kanamycin A derivative are different in their degree of affinity to the cation-exchange resin. Such fractions of the eluate containing the desired N-acylated, protected kanamycin A derivative (Compound 2) which has been eluted separately from the zinc cation can thus be collected together. When these fractions are combined together and concentrated, the desired N-acylated, protected kanamycin A derivative (Compound 2) is obtained.

Stage 2 of the particular procedure according to the above Chart is to protect preferentially the 3''-amino group of Compound 2 by acylating it with a trifluoroacetyl group while retaining the free 1-amino group of Compound 2. The acylation reagent used to this end is ethyl trifluoroacetate in the procedure of the Chart, though a trihaloalkanoic acid ester may be used to that end, in general. This preferential 3''-N-acylation may be effected at a temperature of from −20° C. to 50° C., preferably of from 0° C. to ambient temperature. In this way, there is prepared such a 3,6',3''-tri-N-protected derivative of 2',3'-dideoxykanamycin A (Compound 3) in which the 1-amino group remains free but all the other amino groups, inclusive of the 3''-amino group, have been protected.

Stage 3 is to acylate the 1-amino group of Compound 3 by reacting it with an N-protected ω-amino-α-hydroxyalkanoic acid represented by the formula

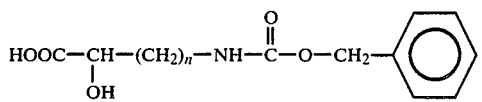

(III'')

wherein n is 1 or 2, or such a reactive carboxylic acid derivative thereof which is a functional equivalent of said alkanoic acid compound (III''). The reactive carboxylic acid derivative of the alkanoic acid compound (III'') may preferably be 4-N-benzyloxycarbonyl-L-4-amino-2-hydroxybutyric acid N-hydroxysuccinimide ester or 3-N-benzyloxycarbonyl-L-3-amino-2-hydroxypropionic acid N-hydroxysuccinimide ester. In this way, Stage 3 gives the 1-N-acylated product (Compound 4). The 1-N-acylation reaction may be effected using DMF, THF, lower alkanol such as methanol, ethanol or an aqueous one of these solvents as the reaction medium and suitably at a reaction temperature of from 0° C. to 30° C.

Stage 4 is the final step to remove the remaining protective groups from Compound 4. For the deprotection purpose, the 3''-N-trifluoroacetyl group may be cleaved at first from Compound 4 in a known manner by hydrolysis which may suitably effected in the presence of a base such as $NH_4OH$, $NaOH$ and $Na_2CO_3$. The benzyloxycarbonyl groups (Z) may subsequently be cleaved by a conventional catalytic hydrogenolysis in the presence of a known hydrogenolysis catalyst such as palladium. The desired compound (I) is thus obtained according to the particular embodiment of the process of this invention as illustrated in the Chart.

This invention is now illustrated with reference to the following Examples to which this invention is not limited.

EXAMPLE 1

(1) Production of 3,6'-di-N-benzyloxycarbonyl-2',3'-dideoxykanamycin A

2',3'-Dideoxykanamycin A (9.0 g, 19.9 milimol.) and zinc acetate dihydrate (24.1 g, 109.8 milimol.) were dissolved in a mixture of water (15.3 ml) and DMF (153 ml). To the resulting solution was added N-(benzyloxycarbonyloxy)-succinimide (11.88 g, 47.7 milimol.) under ice-cooling and stirring. The mixture obtained containing the 2',3'-dideoxykanamycin A-zinc complex as formed, together with the benzyloxycarbonylation reagent, was stirred for 1 hour under ice-cooling and then overnight at ambient temperature to effect the N-benzyloxycarbonylation of the non-chelated amino groups of the zinc complex. The reaction solution was then distilled under reduced pressure to remove partly the solvent therefrom. The resulting residue (as a yellow colored syrup) was taken up into 400 ml of 50% aqueous dioxane (a mixture of dioxane and water at 1:1 by volume) and the solution was passed through a column of a cation-exchange resin, Amberlite CG-50 (H+-form, 600 ml) for the adsorption of the kanamycin A compound. The resin column was washed with 2.7 l of 50% aqueous dioxane and then eluted with 50% aqueous dioxane containing 1N ammonium hydroxide to effect the complete removal of the zinc cation and the chromatographic separation of the titled compound. The desired fractions of the eluate were collected, combined together and concentrated to dryness under reduced pressure to give the titled compound in a yield of 11.2 g (78.3%). This product showed the following properties:

m.p. 203°–218° C.; $[\alpha]_D^{22} +76.3°$ (c 0.7, DMF).

Elemental analysis: Calcd. for $C_{34}H_{48}N_4O_{13}$, $H_2O$: C 55.26, H 6.83, N 7.58%. Found: C 55.48, H 6.61, N 7.44%.

(2) Production of 1-N-(L-4-amino-2-hydroxybutyryl)-2',3'-dideoxykanamycin A

The product of the above procedure (1) (5.1 g, 7.1 milimol.) was dissolved in 70 ml of DMF, to which was then added 2.0 ml of ethyl trifluoroacetate. The mixture was stirred at ambient temperature for 30 minutes to effect the preferential 3''-N-trifluoroacetylation. The reaction solution was distilled under reduced pressure to remove the solvent therefrom, and the resulting yellow-colored syrupy residue was dissolved in 140 ml of 50% aqueous THF (THF-water, 1:1 by volume). To the resulting solution containing the 3,6'-di-N-benzyloxycarbonyl-3''-N-trifluoroacetyl-2',3'-dideoxykanamycin A as formed were added sodium carbonate (1.8 g) and then 4-N-benzyloxycarbonyl-L-4-amino-2-hydroxybutyric acid N-hydroxysuccinimide ester (3.7 g, 10.6 milimol.), followed by agitating the whole mixture for 15 minutes at ambient temperature to effect the 1-N-acylation of the N-protected kanamycin A compound. To the reaction solution so obtained was added 100 ml of 28% aqueous ammonia, followed by stirring the mixture at ambient temperature overnight to effect the hydrolysis (for removal of the 3″-N-trifluoroacetyl group). The reaction mixture obtained was then distilled under reduced pressure to remove the solvent therefrom, and the pale yellow-colored powder residue was dissolved in 150 ml of 50% aqueous THF, to which were then added palladium-black (360 mg) and acetic acid (6.5 ml). The catalytic hydrogenolysis was effected at ambient temperature for 4 hours at a hydrogen gas pressure of 1-2 atm. (for removal of the benzyloxycarbonyl groups). The reaction mixture was filtered to remove the catalyst, and the filtrate was adjusted to pH 6.5 by addition of 1N aqueous sodium hydroxide and then passed through a column of Amberlite CG-50 (ammonium-form, 150 ml) for the adsorption of the active substance. The resin column was washed with 500 ml of water and then with 600 ml of 0.2N aqueous ammonia, followed by eluting with 0.5N aqueous ammonia. The eluate was collected in 15 ml-fractions, and the fractions Nos. 25 to 50 containing the desired 1-N-acylation product were combined together and concentrated under reduced pressure to dryness to afford the titled compound as desired in a yield of 2.25 g (58%).

This product showed the following properties:

m.p. 197°-211° C. (with decomposition); $[\alpha]_D^{22} +91.3°$ (c 0.9, H$_2$O).

Elemental analysis: Calcd. for C$_{22}$H$_{43}$N$_5$O$_{11}$,2H$_2$O: C 44.80, H 8.05, N 11.88%. Found: C 45.28, H 7.84, N 12.13%.

EXAMPLE 2

Production of 1-N-(L-3-amino-2-hydroxypropionyl)-2′,3′-dideoxykanamycin A

The product of the Example 1 (1), namely 3,6′-di-N-benzyloxycarbonyl-2′,3′-dideoxykanamycin A (5.1 g, 7.1 milimol.) was dissolved in 70 ml of DMF, to which was then added 2.0 ml of ethyl trifluoroacetate, followed by stirring the whole mixture at ambient temperature for 20 minutes to effect the preferential 3″-N-trifluoroacetylation. The reaction solution was distilled under reduced pressure to remove the solvent therefrom, and the yellow-colored syrupy residue was dissolved in 140 ml of 50% aqueous THF. To the resulting solution containing the 3,6′-di-N-benzyloxycarbonyl-3″-N-trifluoroacetyl-2′,3′-dideoxykanamycin A as produced were added sodium carbonate (1.8 g) and then 3-N-benzyloxycarbonyl-L-3-amino-2-hydroxypropionic acid N-hydroxysuccinimide ester (3.6 g, 10.6 milimol.). The resulting mixture was then stirred at ambient temperature for 15 minutes.

The reaction mixture was mixed with 100 ml of 28% aqueous ammonia, followed by stirring at ambient temperature overnight to effect the hydrolysis for removal of the 3″-N-trifluoroacetyl group. The reaction solution was distilled under reduced pressure to remove the solvent, and the pale yellow-colored powder residue was dissolved in 150 ml of 50% aqueous THF. To the solution obtained were added palladium-black (360 mg) and acetic acid (6.5 ml), and the catalytic hydrogenolysis was effected at ambient temperature for 4 hours at a hydrogen gas pressure of 1 atm. for removal of the benzyloxycarbonyl group. The reaction mixture was filtered to remove the catalyst, and the filtrate was adjusted to pH 6.5 by addition of 1N aqueous NaOH and passed through a column of Amberlite CG-50 (NH$_4$+-form, 150 ml) for adsorption of the active substance. This resin column was then washed with 500 ml of water and eluted with 0.2N aqueous ammonia. The eluate was collected in 15 ml-fractions and the active fractions Nos. 20 to 43 were combined together and concentrated under reduced pressure to dryness to give the titled compound in a yield of 1.3 g (34.4%). This product showed the following properties:

m.p. 220°-228° C. (with decomposition); $[\alpha]_D^{22} +97.2°$ (c 0.7, H$_2$O).

Elemental analysis: Calcd. for C$_{21}$H$_{41}$N$_5$O$_{11}$, H$_2$O: C 45.22, H 7.79, N 12.56%. Found: C 45.44, H 7.61, N 12.66%.

What we claim is:

1. A compound represented by the formula

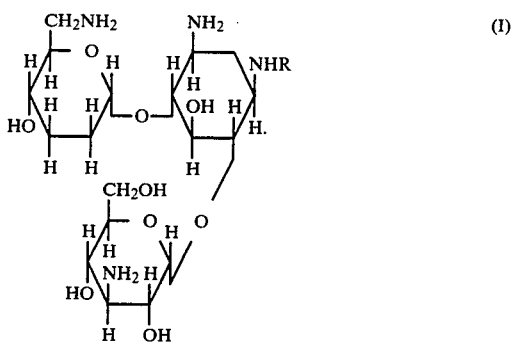

wherein R denotes an L-3-amino-2-hydroxypropionyl group or an L-4-amino-2-hydroxybutyryl group, and a pharmaceutically acceptable acid addition salt thereof.

2. A compound of claim 1 which is 1-N-(L-3-amino-2-hydroxypropionyl)-2′,3′-dideoxykanamycin A or a pharmaceutically acceptable acid addition salt thereof.

3. A compound of claim 1 which is 1-N-(L-4-amino-2-hydroxybutyryl)-2′,3′-dideoxykanamycin A or a pharmaceutically acceptable acid addition salt thereof.

4. An antibacterial composition comprising as the active ingredient antibacterially effective amounts of the compound of the formula (I) as defined in claim 1 or a pharmaceutically acceptable acid addition salt thereof, in combination with a carrier for the active ingredient compound.

* * * * *